United States Patent
Chen et al.

(10) Patent No.: US 6,774,231 B2
(45) Date of Patent: Aug. 10, 2004

(54) METHOD FOR THE PREPARATION OF OXAZOLIDINONES

(75) Inventors: Jiong Jack Chen, Kalamazoo, MI (US); Cuong V. Lu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/122,853

(22) Filed: Apr. 15, 2002

(65) Prior Publication Data

US 2003/0004160 A1 Jan. 2, 2003

Related U.S. Application Data

(60) Provisional application No. 60/285,588, filed on Apr. 20, 2001.

(51) Int. Cl.[7] .................. C07D 295/073; C07D 295/00; A61K 31/54; A61P 31/00
(52) U.S. Cl. ............................. 544/59; 544/60; 564/305
(58) Field of Search ...................... 544/59, 60

(56) References Cited

U.S. PATENT DOCUMENTS

| | | | | |
|---|---|---|---|---|
| 3,585,182 A | 6/1971 | Straley et al. | ............... | 260/157 |
| 5,880,118 A | 3/1999 | Barbachyn et al. | ......... | 514/211 |
| 5,968,962 A | 10/1999 | Thomas et al. | ............. | 514/376 |
| 5,981,528 A | 11/1999 | Gravestock | ................. | 514/252 |

FOREIGN PATENT DOCUMENTS

| | | |
|---|---|---|
| JP | 63148259 | 6/1988 |
| WO | WO95/07271 | 3/1995 |
| WO | WO97/10223 | 3/1997 |
| WO | WO01/98297 | 12/2001 |
| WO | WO02/30395 | 4/2002 |

OTHER PUBLICATIONS

Barbachyn, et al., "Identification of a Novel Oxazolidinone (U–100480) with Potent Antimycobacterial Activity," *J. Med. Chem.*, 1996, 39, pp. 680–685.

XP–002204089, 4–phenyl–thiomorpholine 1,1,–dioxide, 1988, *Beilstein Institute zur Förderung der Chemischen Wissenschaften*, Database Accession No. 154714, Reaction 1 of 6 Abstract, J. Chem Soc, 1949; pp. 2433–2440.

XP–002204090, "4–(2–chloro–phenyl)–thiomorpholine 1,1–dioxide," 1991, *Beilstein Institute zur Förderung der Chemischen Wissenschaften*, Database Accession No. 4439946, Reaction Abstract, Synthesis, vol. 5, 1982, pp. 417–419.

*Primary Examiner*—Mark L. Berch
*Assistant Examiner*—Kahsay Habte
(74) *Attorney, Agent, or Firm*—Lucy X. Yang

(57) ABSTRACT

The present invention relates to a process for making a compound of structure 4

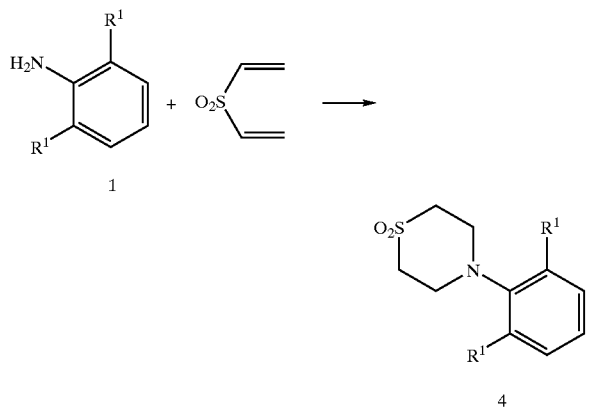

which comprises reacting a compound of structure 1 with vinyl sulfone in the presence of a Lewis-acid at a temperature in a range of from 40° C. to 170° C., wherein each $R^1$ is independently H, fluoro, chloro or bromo.

22 Claims, No Drawings

METHOD FOR THE PREPARATION OF OXAZOLIDINONES

CROSS REFERENCE TO RELATED APPLICATION

This application claims the benefit of the following provisional application: U.S. Ser. No. 60/285,588, filed Apr. 20, 2001, under 35 USC 119(e)(i), which is incorporated herein by reference in its entirety.

FIELD OF THE INVENTION

The present invention relates to a method for the production of N-({(5S)-3-[4-(1,1-dioxido-4-thiomorpholinyl)-3,5-difluorophenyl]-2-oxo-1,3-oxazolidin-5-yl}methyl) acetamide or its pharmaceutically acceptable salt.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, gram-negative aerobic bacteria such as *H. influenzae* and *M. catarrahlis*, as well as anaerobic organisms such as bacteroides and clostridia species, and acid-fast organisms such as *Mycobacterium tuberculosis* and *Mycobacterium avium*.

The present invention provides a novel method for the production of N-({(5S)-3-[4-(1,1-dioxido-4-thiomorpholinyl)-3,5-difluorophenyl]-2-oxo-1,3-oxazolidin-5-yl}methyl)acetamide. This compound has broad coverage against Gram-positive organisms. In particular, it demonstrates beneficial efficacy for treating infections caused by resistant pathogens. In addition, the present invention provides novel intermediates useful for the preparation of N-({(5S)-3-[4-(1,1-dioxido-4-thiomorpholinyl)-3,5-difluorophenyl]-2-oxo-1,3-oxazolidin-5-yl}methyl)acetamide.

INFORMATION DISCLOSURE

U.S. Pat. No. 5,880,118 discloses substituted oxazine and thiazine oxazolidinone antimicrobials.

U.S. Pat. No. 6,968,962 discloses phenyloxazolidinones having a C—C bond to 4–8 membered heterocyclic rings.

U.S. Pat. No. 5,981,528 discloses antibiotic oxazolidinone derivatives.

U.S. Pat. application Serial No. 60/236595 discloses N-({(5S)-3-[4-(1,1-dioxido-4-thiomorpholinyl)-3,5-difluorophenyl]-2-oxo-1,3-oxazolidin-5-yl}methyl) acetamide.

*J. Chem. Soc.* 1949, 2433–2440 and U.S. Pat. No. 3,585,182 discloses the formation of thiomorpholine, 1,1-dioxide from vinyl sulfone and aniline. Due to the sluggishness of the double Michael addition, excess aniline is needed to achieve reasonable yield. The present invention uses a Lewis acid as a catalyst to form a compound of structure (4) as shown below wherein the reaction needs only equal equivalence of vinyl sulfone and aniline.

DETAILED DESCRIPTION OF THE INVENTION

The N-({(5S)-3-[4-(1,1-dioxido-4-thiomorpholinyl)-3,5-difluorophenyl]-2-oxo-1,3-oxazolidin-5-yl}methyl) acetamide is prepared according to Scheme I and examples described herein below.

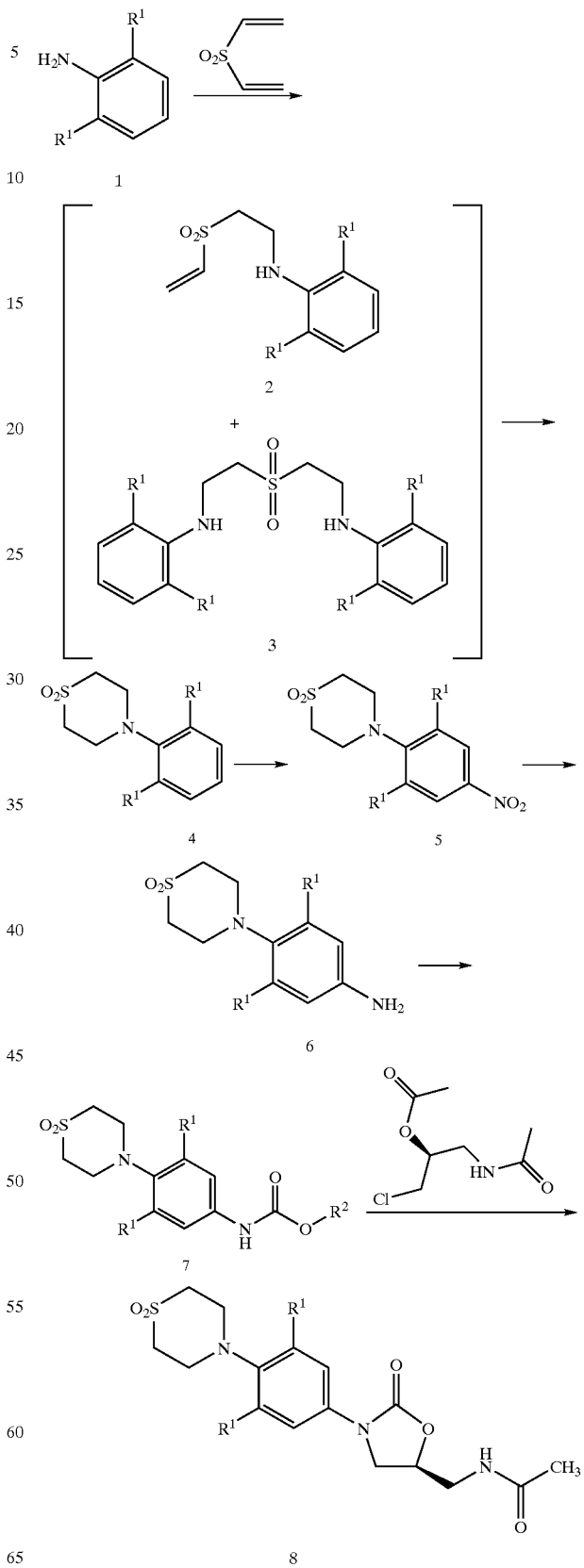

SCHEME I

In Scheme 1, each $R^1$ is independently hydrogen, fluorine, chlorine or bromine atom. Preferably both $R^1$ are fluorine atoms. $R^2$ is a straight and branched alkyl group having one to twelve carbon atoms, which may be substituted by a phenyl group. As shown in step one, a Lewis-acid such as aluminum chloride mediates a double Michael addition between vinyl sulfone and an aniline of structure 1 to form a compound of structure 4 via compounds of structures 2 and 3. The reaction occurs at a temperature in a range of from 40° C. to 170° C., preferably at between 100° C. and 110° C. for reactions using solvents, at between 140–160° C. for reactions with no solvents. The reaction solvent can be any solvent that does not adversely affect the reaction, but preferably is halogenated aliphatics, halogenated aromatics or hydrocarbon aromatics, and more preferably is 1,2-dichloroethane, chlorobenzene or toluene. Lewis acids of the present invention includes, but not limits, strong acids and lanthanide triflates, preferably is $AlCl_3$, $FeCl_3$, $BiCl_3$, $SnCl_2$, $ZnCl_2$, TfOH, Yb(OTf)$_3$, and more preferably is $AlCl_3$, TfOH or Yb(OTf)$_3$. The double Michael addition can also be mediated with weak acids, such as AcOH, $H_3PO_4$ or trfluoroacetic acid. The preferred weak acids is $H_3PO_4$. The reaction temperature can be between 60–180° C., but preferably at 110–150° C.

Transformation of 4 to 5 can be accomplished by a procedures well known to one skilled in the art. For example, a number of standard nitration conditions, such as nitric acid, a mixture of acetyl chloride and silver nitrate, or nitric acid with a Lewis acid as a catalyst may be utilized. However, economically efficient nitric acid based conditions and nitric acid alone as a nitration agent are preferred reaction routes. The reaction solvent can be any solvent that does not adversely affect the reaction, but preferably carboxylic acid, carboxylic anhydride and halogenated aliphatics, and more preferably acetic acid. The equivalents of nitric acid can be between 1–20, but preferably between 5–10. The reaction temperature can be between 0–60° C., but preferably between 10–30° C.

Transformation of 5 to 6 can be accomplished by a procedures well known to one skilled in the art. For example, a number of reduction conditions, such as hydrogenation with metal catalysts, reduction with iron and iron (II) sulfate may be utilized. However, hydrogenation with metal catalysts, and hydrogenation with Ni-based catalysts are preferred reaction routes. The reaction solvent can be any solvent that does not adversely affect the reaction, but preferably halogenated aliphatics, alcohols, aliphatic esters and THF, and more preferably THF. The equivalents of Ni-based catalyst can be between 5–40%, but preferably between 10–20%. The reaction temperature can be between 0–100° C., but preferably between 35–45° C.

Ttransformation or 6 to 7 can be accomplished by a procedures well known to one skilled in the art. For example, a number of carbamate formation conditions, such as haloalkylformate with trialkyl amine as base, haloalkylformate with aqueous metal carbonate as base, or dialkylcarbonate with base may be utilized. However, haloalkylformate with base, and haloalkylformate with aqueous potassium carbonate as base are preferred routes. The reaction solvent can be any solvent that does not adversely affect the reaction, but preferably halogenated aliphatics, alcohols, aliphatic esters and THF, and more preferably THF. The equivalents of potassium carbonate can be between 1–10, but preferably between 2–3. The equivalents of haloalkylformate can be between 1–4, but preferably between 1.2–2.0. The reaction temperature can be between 0–100° C., but preferably between 45–55° C.

Finally, reacting 7 with an (S)-chloroacetamidoacetoxypropane in the presence of a base, a lithium cation, a nucleophile and a solevnt provides compound 8.

Alternatively, the compound of structure may be prepared according to the procedures illustrated in Scheme II.

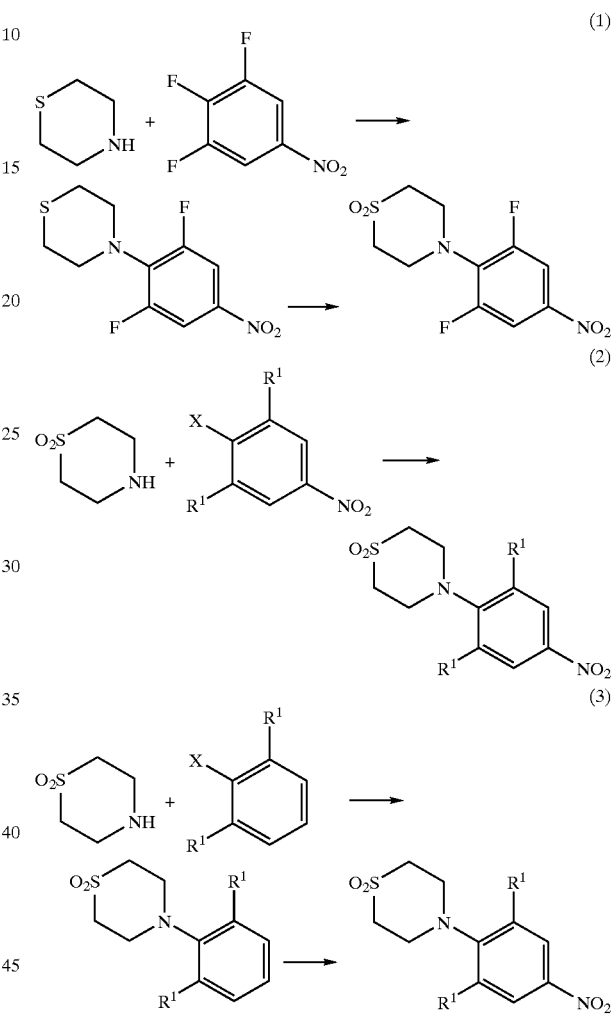

SCHEME II

In Scheme II, X refers to a chlorine, bromine or iodine atom. Each $R^1$ is the same as defined above.

In equation (1): In step 1, the reaction occurs in the presence of a base and in a solvent system. The bases can be any bases that neutralize HF, but preferably trialkylamine, and more preferably is triethylamine. The reaction solvent can be any solvent that does not adversely affect the reaction, but preferably is halogenated aliphatics, and more preferably is methylene chloride. In step 2, the conversion requires an oxidant and in the presence of a solvent system. The oxidants can be any oxidants that oxidize sulfide to sulfone, but preferably oxone. The reaction solvent can be any solvent that does not adversely affect the reaction, but preferably is halogenated aliphatics mixed with water, and more preferably is methylene chloride mixed with water.

In equation (2): The reaction occurs in the presence of a base, a catalyst, and a solvent system. The Pd-based catalysts can be any catalysts that facilitate the formation of a nitrogen and carbon bond, but preferably Pd[O] or Pd[II]

catalysts, and more preferably is Pd(OAc)$_2$. The ligand can be any ligands that assist Pd catalyst for the formation of a nitrogen and carbon bond, but preferably phosphorus based catalysts, and more preferably is 2-(dicyclohexylphosphino) biphenyl and 2-(di-t-butylphosphino)biphenyl. The reaction solvent can be any solvent that does not adversely affect the reaction, but preferably is hydrocarbon aromatics, and more preferably is toluene.

In equatoin (3): In step 1, the conditions are similar to equation (1). In step 2, the reaction requires a nitration agent. The nitration agent can be any nitration reagent that nitrate an aromatic ring. The reaction solvent can be any solvent that does not adversely affect the reaction, but preferably is carboxylic acid and halogenated aliphatics, and more preferably is acetic acid.

Definitions

All temperatures are in degrees Centigrade.
TLC refers to thin-layer chromatography.
HPLC refers to high pressure liquid chromatography.
THF refers to tetrahydrofuran.
DMF refers to dimethylformamide.
DMAC refers to dimethylacetamide.
DMSO refers to dimethylsulfate.
Chromatography (column and flash chromatography) refers to purification/separation of compounds expressed as (support, eluent). It is understood that the appropriate fractions are pooled and concentrated to give the desired compound(s).
NMR refers to nuclear (proton) magnetic resonance spectroscopy, chemical shifts are reported in ppm ($\delta$) downfield from tetramethylsilane.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.
When solvent pairs are used, the ratios of solvents used are volume/volume (v/v).
When the solubility of a solid in a solvent is used the ratio of the solid to the solvent is weight/volume (wt/v).

EXAMPLES

Example 1

Preparation of 4-(2,6-difluorophenyl)thiomorpholine 1,1-dioxide (Scheme I, structure 4, both $R^1$ are fluorine atoms)

Aluminum chloride (310 g, 2.3 mol) is added to chlorobenzene (2.5 L) to give a cloudy green suspension. Vinyl sulfone (230 mL, 2.3 mol) is added via a funnel. 2,6-Difluoroaniline (250 μL, 2.3 mol) is added a via funnel. The light brown solution is heated to 110° C. Upon completion, the heat is removed and the black solution is self-cooled to 70° C. The reaction mixture is quenched in methylene chloride (4 L) and ice water (5 L). The aqueous phase is extracted with methylene chloride. The combined organic layers are concentrated and added branched octane (3 L), and then cooled to 0° C. for 30 minutes. The solids are filtered and washed with branched octane (2×500 L). The crude black solids are dissolved into methylene chloride (3 L) and then loaded onto a SiO$_2$ plug (1.8 kg). The column is eluted with dichloromethane (16L) until clear. The methylene chloride solution is concentrated to give light brown solids (387 g or 68% yield). The solids are dissolved in hot ethyl acetate (3 L) followed by the addition of hexanes (900 mL). The black solution is self-cooled to room temperature overnight. The light amber crystal needles are filtered and washed with hexanes (4×250 mL). The solids are dried in vacuo at 50° C. overnight to give 314 g of the title compound (55% recystallized yield 1$^{st}$ crop).

$^1$H NMR (CDCl$_3$) ($\delta$): 7.08 (m, 1H), 6.91 (m, 2H), 3.67 (m, 4H), 3.18 (m, 4H).

Examples 2

Preparation of N-(2-{[2-(2,6-difluoroanilino)ethyl]sulfonyl}ethyl)-2,6-difluoroaniline (3) and (2-ethenesulfonylethyl)-2,6-difluorophenylamine (2) (Scheme I, structures 3 and 2, both $R^1$ are fluorine atoms)

About 5–6 hours after the reaction commenced in example 1, a small portion of the mixture is separated and purified by chromatography to give structure 2 and 3.

$^1$H NMR (CDCl$_3$) ($\delta$)/compound (3): 6.80 (m, 4H), 6.70 (m, 2H), 3.85 (t, 4H), 3.32 (t, 4H). $^1$H NMR (CDCl$_3$) ($\delta$)/compound 2: 6.83 (m, 2H), 6.60 (m, 2H), 6.40 (m, 1H), 6.11 (d, 1H), 3.83 (t, 2H), 3.26 (t, 2H).

Example 3

Preparation of 4-(2,6-difluoro-4-nitrophenyl)thiomorpholine 1,1-dioxide (Scheme I, structure 5, both $R^1$ are fluorine atoms)

To a suspension of the product of example 1 (300 g, 1.21 mol) in 3 L of acetic acid, nitric acid (255 mL, ca. 6 mol, fuming, 90%) is added over 30 min at room temperature. Yellow precipitate is formed within minutes and increases over time. The reaction is kept at room temperature for 18 hours, before it is poured into 6 L of water. After stirred for 2 hours, the yellow suspension is filtered. The precipitate is washed with water (1.5 L×3) and EtOH (0.5 L×2) and dried in oven at 50° C. overnight to give 333 g (94%) of the title compound as a solid.

$^1$H NMR (DMSO-d$_6$) ($\delta$): 8.05 (m, 2H), 3.69 (m, 4H), 3.26 (m, 4H).

Example 4

Preparation of 4-(1,1-dioxido-4-thiomorpholinyl)-3,5-difluoroaniline (Scheme I, structure 6, both $R^1$ are fluorine atoms)

To an autoclave is added the product of example 3 (7.0 kg, 24 moles, 1.0 eq). Raney Nickel (1.4 kg) is activated and suspended in 4 L of THF. The slurry is added to the autoclave followed by additional THF (66 L). The mixture is heated at 40° C. and under 40 psi H$_2$ till completion. The mixture is filtered and the filtrate is directly used in the next step. A small portion of the filtrate is concentrated and recrystallized in isopropanol to give the title compound.

$^1$H NMR (DMSO-d$_6$) ($\delta$): 6.17 (m, 2H), 5.35 (s, 2H), 3.32 (m, 4H), 3.15 (m, 4H Example 5

Preparation of isobutyl 4-(1,1-dioxido-4-thiomorpholinyl)-3,5-difluorophenylcarbamate (Scheme I, structure 7, both $R^1$ are fluorine atoms)

To the 400 L glass-lined reactor containing the product of example 4 in THF (12.6 kg, 48 moles, 1.0 eq) solutions is added 47% potassium carbonate solution (14.1 kg, 48 moles, 1.0 eq). The mixture is heated to ca 45° C. Isobutyl chloroformate (7.2 kg, 53 moles, 1.1 eq) is added to the mixture while maintaining a reaction temperature between 45° C. and 55° C. The reaction is stirred at 45° C. and 55° C. Once deemed complete, the reaction is quenched by slowly adding water (45 L) over 15 minutes. The reaction mixture is cooled to 25° C. and the phases separated. The THF solution is swapped to a 150 L of isopropanol and 50 L of water suspension. The slurry is slowly cooled to 5° C. Then, the yellow slurry is filtered and the cake washed with cold isopropanol (2×30 L). The yellow solids are dried with 60° C. $N_2$ to give the title compound as a solid (14.2 kg, 82% yield).

$^1$H NMR (CDCl$_3$) (δ): 7.02 (m, 2H), 6.81 (s, 1H), 3.95 (d, 2H), 3.60 (m, 4H), 4H), 1.97 (m, 1H), 0.94 (d, 6H).

Example 6

Preparation of N-({(5S)-3-[4-(1,1-dioxido-4-thiomorpholinyl)-3,5-difluorophenyl]-2-oxo-1,3-oxazolidin-5-yl}methyl)acetamide (Scheme I, structure 8, both R$^1$ are fluorine atoms)

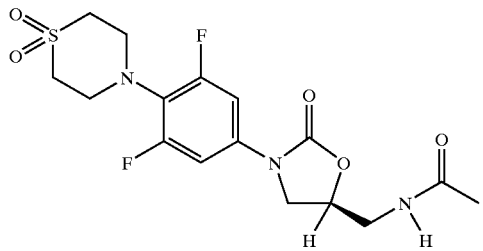

To a dry, nitrogen purged 400 L glass-lined reactor is added LiOtBu (6.96 kg, 87 moles, 3.0 eq), the product of example 5 (10.50 kg, 29 moles, 1.0 eq), and branched octane (70 L). The slurry is cooled to ca 20° C. Then, DMF (10 L) is slowly added over 25 min and the slurry is stirred for 30 min. Methanol (1.86 kg, 58 moles, 2.0 eq) is slowly added over 25 min. The line is rinsed with branched octane (1 L) and the slurry stirred at ca 15° C. To a dry, nitrogen purged 200 L glass-lined reactor is added (S)-N-[2-(acetyloxy)-3-chloropropyl]acetamide (11.22 kg, 58 moles, 2.0 eq) and DMF (9.4 L). (S)-N-[2-(acetyloxy)-3-chloropropyl] acetamide is known in the art and can be prepared according to the procedures described in Tetrahedron Letters, Vol. 37, No. 44, pp. 7937–7940 and WO 9924393. The solution is stirred at ca 25° C. to 30° C. for 1 hours for complete solid dissolution. This light yellow solution is slowly added to the slurry over 1.5 hours while maintaining the temperature between 15° C. and 16° C. The line is rinsed with branched octane (20 L). At 15 h, HPLC assay indicated ca 94% conversion. Glacial acetic acid (3.48 kg, 58 moles, 2.0 eq) is slowly added over 30 min followed by a line rinse of methanol (14 L). The biphasic solution is stirred for 1 hour and then separated. The upper organic phase is re-extracted with methanol (14 L) and DW water (4.7 L). The layers are separated. To the combined lower aqueous organic phase is added CH$_2$Cl$_2$ (32 L) and DW water (32 L). The biphasic solution is stirred and the layers separated. The aqueous phase is re-extracted twice with CH$_2$Cl$_2$ (2×11 L). The combined organic layers are then distilled under vacuum to ca 70 L and n-BuOH (210 L) is then slowly added while maintaining distillation and a total volume of ca 80 L. Once the addition is complete, the slurry is concentrated to a final volume of ca 58 L and cooled to ca 40° C. Isopropyl alcohol (53 L) is slowly added to the slurry over 30 min and then slowly cooled further to 0° C. over 2 hours. After stirring for 30 min, the solids are filtered and the cake is washed three times with cold isopropanol (3×53 L). The yellow solids are dried with 60° C. $N_2$ to give the title compound as a solid (9.3 kg, 79% yield).

$^1$H NMR (DMSO-$\delta_6$) 1.83 (s, 3H), 3.20–3.24 (m, 4H), 3.40 (t, J=5.6 Hz, 2H) 3.47–3.51 (m, 4H), 3.70 (dd, J=9.0 Hz, J=7.9 Hz, 1H), 4.09 (t, J=9.0 Hz, 1H), 4.69–4.78 (m, 1H), 7.29 (s, 1H), 7.32 (s, 1H), 8.21 (t, J=5.6 Hz, 1H).

What is claimed is:

1. A process for making a compound of structure 4

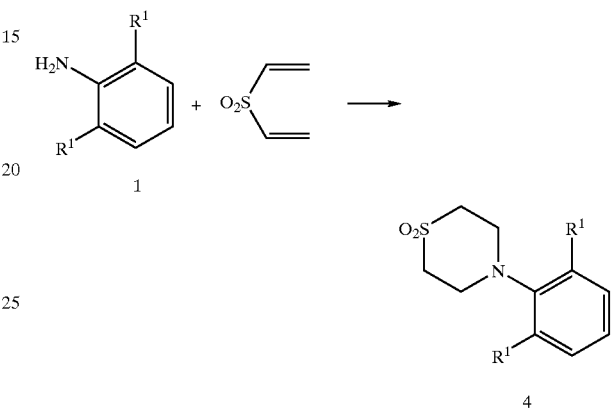

which comprises reacting a compound of structure 1 with vinyl sulfone in the presence of a Lewis-acid at a temperature in a range of from 40° C. to 170° C., wherein each R$^1$ is independently H, fluoro, chloro or bromo.

2. The method of claim 1 wherein R$^1$ is fluoro.

3. The method of claim 1 or 2 wherein the Lewis-acid is FeCl$_3$, BiCl$_3$, SnCl$_2$, or ZnCl$_2$.

4. The method of claim 1 or 2 wherein the Lewis-acid is TfOH or Yb(OTf)$_3$.

5. The method of claim 1 or 2 wherein the Lewis-acid is AlCl$_3$.

6. The method of claim 1 or 2 wherein the Lewis-acid is AcOH, or trifluoroacetic acid.

7. The method of claim 1 or 2 wherein the Lewis-acid is H$_3$PO$_4$.

8. A method for using a compound of structure 4 for the preparation of a pharmaceutically active compound 8 or a pharmaceutically acceptable salt thereof,

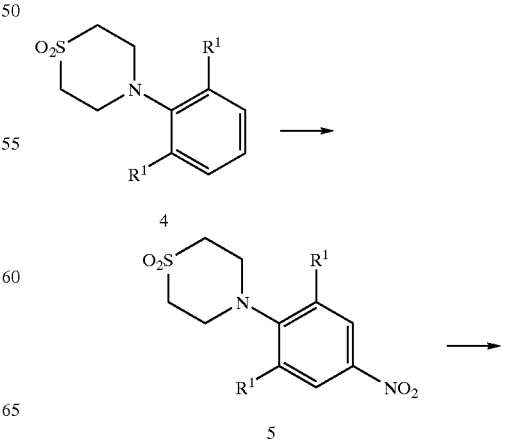

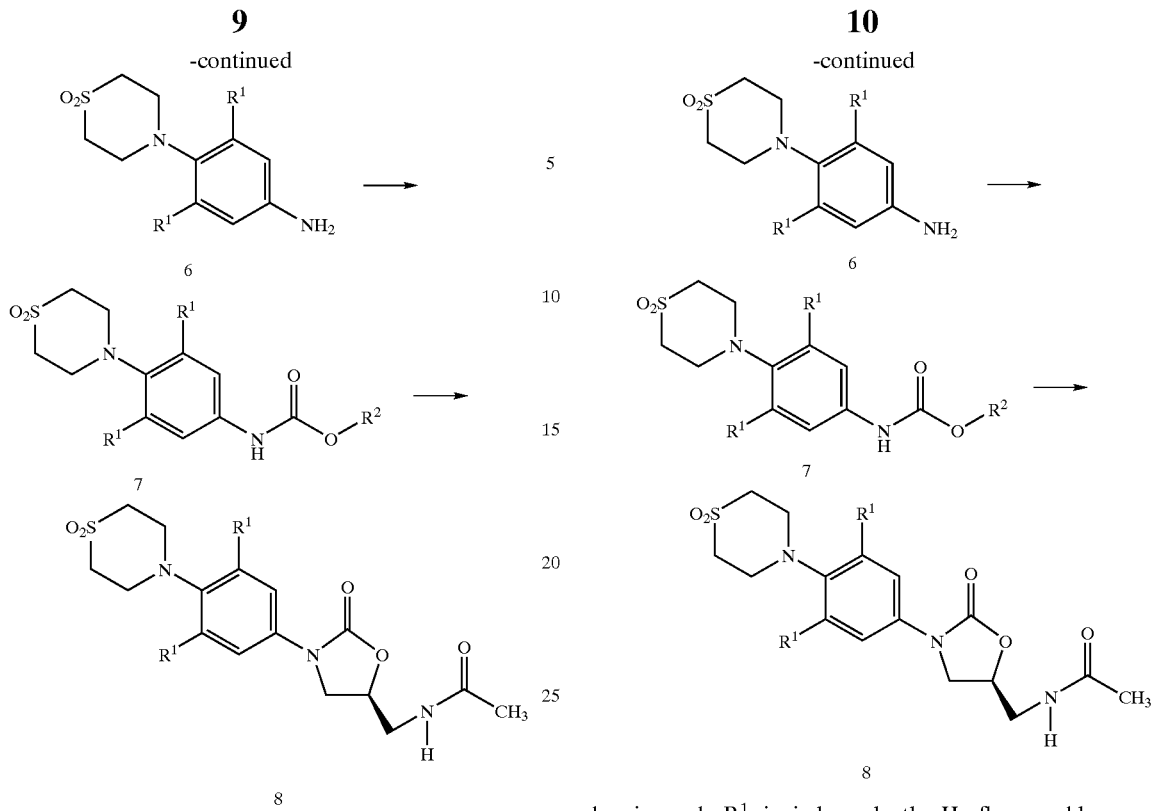

wherein each $R^1$ is independently H, fluoro, chloro or bromo atom; $R^2$ is a straight and branched alkyl group having one to twelve carbon atoms, optionally substituted by a phenyl group; which comprises steps of:

(a) nitration of a compound of structure 4 to a compound of structure 5, (b) reduction of a compound of structure 5 to a compound of structure 6, (c) acylation of a compound of structure 6 to a compound of structure 7, and (d) reacting a compound of structure 7 with (S)-N-[2-(acetyloxy)-3-chloropropyl]acetamide.

9. The method of claim 8 wherein $R^1$ is fluoro.

10. The method of claim 8 or 9 wherein $R^2$ is isobutyl.

11. A method for preparing a pharmaceutically active compound 8 or a pharmaceutically acceptable salt thereof,

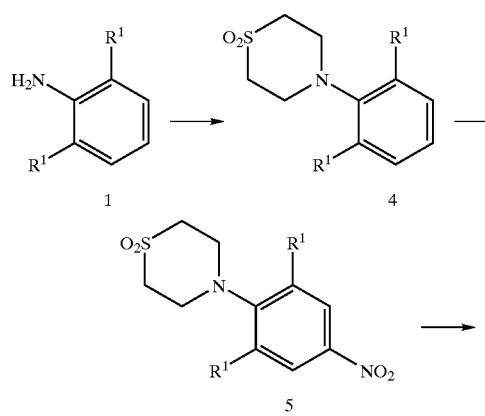

wherein each $R^1$ is independently H, fluoro, chloro or bromo; $R^2$ is a straight and branched alkyl group having one to twelve carbon atoms, optionally substituted by a phenyl group; which comprises steps of:

(a) reacting a compound of structure 1 with vinyl sulfone in the presence of a Lewis-acid at a temperature in a range of from 40° C. to 170° C., (b) nitration of a compound of structure 4 to a compound of structure 5, (c) reduction of a compound of structure 5 to a compound of structure 6, (d) acylation of a compound of structure 6 to a compound of structure 7, and (e) reacting a compound of structure 7 with (S)-N-[2-(acetyloxy)-3-chloropropyl]acetamide.

12. The method of claim 11 wherein $R^1$ is fluoro.

13. The method of claim 11 or 12 wherein the Lewis-acid is $FeCl_3$, $BiCl_3$, $SnCl_2$, or $ZnCl_2$.

14. The method of claim 11 or 12 wherein the Lewis-acid is TfOH or $Yb(OTf)_3$.

15. The method of claim 11 or 12 wherein the Lewis-acid is $AlCl_3$.

16. The method of claim 11 or 12 wherein the Lewis-acid is AcOH, or trifluoroacetic acid.

17. The method of claim 11 or 12 wherein the Lewis-acid is $H_3PO_4$.

18. The method of claim 11 or 12 wherein $R^2$ is isobutyl.

19. An intermediate useful for the preparation of a pharmaceutically active compound comprising 4-(2,6-difluorophenyl)thiomorpholine 1,1-dioxide.

20. An intermediate useful for the preparation of a pharmaceutically active compound consisting of 4-(2,6-difluoro-4-nitrophenyl)thiomorpholine 1,1-dioxide.

21. An intermediate useful for the preparation of a pharmaceutically active compound consisting of 4-(1,1-dioxido-4-thiomorpholinyl)-3,5-difluoroaniline.

22. An intermediate useful for the preparation of a pharmaceutically active compound consisting of isobutyl 4-(1,1-dioxido-4-thiomorpholinyl)-3,5-difluorophenylcarbamate.

* * * * *